United States Patent [19]
Paglin et al.

[11] Patent Number: 5,172,859
[45] Date of Patent: Dec. 22, 1992

[54] LIQUID DIFFUSER DEVICE

[76] Inventors: Neriel Paglin, 6 Hazamir St., Ramat-Gan; Eyal Ron, 28 Alumin St., Tel-Aviv, both of Israel

[21] Appl. No.: 730,604

[22] Filed: Jul. 16, 1991

[30] Foreign Application Priority Data

Jul. 19, 1990 [IL] Israel .................................. 95123

[51] Int. Cl.⁵ .............................................. A61L 9/12
[52] U.S. Cl. ........................................ 239/42; 239/39; 239/43
[58] Field of Search ............... 239/37, 39, 42, 43; 43/107, 122, 124, 132.1

[56] References Cited

U.S. PATENT DOCUMENTS

| | | | |
|---|---|---|---|
| 1,818,684 | 8/1931 | Blechman | 239/42 |
| 1,944,375 | 1/1934 | Schneider | 239/42 |
| 1,974,414 | 9/1934 | Dupuy | 239/42 |
| 2,166,969 | 7/1939 | Rooch | 239/42 |
| 2,246,008 | 6/1941 | Rooch | 239/42 |
| 2,481,296 | 9/1949 | Dupuy | 239/42 |
| 2,586,179 | 2/1952 | Rooch | 239/42 |
| 4,526,320 | 7/1985 | Von Philipp et al. | 239/43 |
| 4,537,351 | 8/1985 | Wilson | 239/43 |
| 4,571,880 | 2/1986 | Hayward | 43/122 |
| 4,718,193 | 1/1988 | Rosselli | 43/122 |

Primary Examiner—Andres Kashnikow
Assistant Examiner—William Grant
Attorney, Agent, or Firm—Leonard Bloom

[57] ABSTRACT

A liquid diffuser device is disclosed that includes a liquid holding container having a neck portion that extends from the bottom wall thereof. A base portion is associated with the container, such that the liquid holding container and the base portion are slidably longitudinally movable relative to one another between an uppermost position and a lowermost position. The base portion is provided for tightly sealing the discharge opening of the neck portion. In the uppermost position, the discharge opening is engaged and tightly sealed, so that the flow of liquid from the container through the neck portion is prevented. In the lowermost position, the discharge opening is not sealed, so that the flow of fluid through the discharge opening is permitted.

8 Claims, 4 Drawing Sheets ial state;
LIQUID DIFFUSER DEVICE

FIELD OF THE INVENTION

The present invention generally concerns diffuser devices of the kind in which a liquid is diffused from the surface of an absorber body. Diffusion may be by way of evaporation such as in case of a so-called air purifier and/or the gradual release of an insecticidal vapour or by contact such as in the case of a device for destroying insects.

In the following the background of the invention and the invention itself will be described with reference to the destruction of insects, it being understood that the invention is not confined thereto.

BACKGROUND OF THE INVENTION AND PRIOR ART

Controlling insects is a major problem, both in households as well as in agriculture, horticulture and forestry. While conventionally, control of insects is performed by spraying an area with an insecticide, such a form of control is very often undesirable due to its adverse ecological effects.

In order to circumvent the ecological problems associated with spraying of insecticide, it has been proposed to use diffusers of a poisonous bait liquid. Such diffusers have an absorber body soaked with a liquid comprising an insect attracting agent such as a nutrient or a pheromone, and an insecticide. The insects which are attracted to the absorber body are poisoned and destroyed by the insecticide therein, either upon contact or upon ingestion. One of the major drawbacks of known insecticidal devices of the kind specified is that the absorber body has to be replenished by periodical spraying.

Diffuser devices of the kind specified for use as air purifiers and the like have been described for example in U.S. Pat. Nos. 1,818,684, 2,166,969 and 2,246,008. These known diffuser devices comprise each a liquid container with a discharge opening leading into a skirted dish connected to a sleeve of an absorbent material. The skirted disk is thus fed with liquid from the container whereby the absorbent material is soaked with the liquid which diffuses by evaporation to the surrounding atmosphere. In order to discharge the fluid only when required, i.e. in operation and not during transport or storage, some of the known devices are fitted with a discharge control mechanism. Alternatively, the liquid container may be capped and stored separately of the dish/diffuser sleeve assembly. In operation the liquid container cap is removed, and the container is introduced in inverted position into the dish. Obviously such an operation is cumbersome and also entails spilling of the liquid during assembly.

It is the object of the present invention to provide an improved diffuser device of the kind specified in which the absorber body is automatically replenished during operation.

GENERAL DESCRIPTION OF THE INVENTION

The above objects are achieved in accordance with the present invention by a liquid diffuser device comprising in combination:
i) a liquid holding container having a neck portion extending from an end wall which in operation constitutes the bottom, which neck portion has a discharge opening;
ii) a base portion comprising a cap or a plug adapted to tightly seal the discharge opening of said neck portion and made integral with a skirted dish;
iii) upright retainer means integral with said base portion and designed to engage stop means in said container whereby said skirted dish is arrested in a lowermost position in which the skirted portion of said dish extends above the discharge opening of said neck portion; and
iv) an absorbent material body one end of which is in said skirted dish.

By a preferred embodiment of the present invention the said absorbent material body is a sleeve that envelopes the container.

If desired the device may be adapted for hanging and for that purpose the end wall of the container, which in operation constitutes the top of the device, may be fitted with integral hanger means. The device may also be adapted for placing same on the base portion during operation and for that purpose the said base portion may comprise a combined support-spacer means for supporting the container and keeping it sufficiently spaced so as to leave open the discharge opening thereof.

Diffuser devices according to the invention are particularly suitable for the destruction of insects at home and in agriculture, horticulture and forestry. To this end the said liquid will comprise an insecticide, preferably in combination with an agent for attracting the insects, e.g. a nutrient such as sugar or a pheromone.

Additionally the diffuser devices according to the invention may be used for various other purposes such as, for example, air purifiers.

This invention also provides a container and a base portion adapted for use in said device.

DETAILED DESCRIPTION OF THE DRAWINGS

For better understanding the invention will now be described, by way of example only, with reference to the annexed drawings, it being understood that the invention is not confined thereto. In the drawings.

DESCRIPTION OF A SPECIFIC EMBODIMENT

Figure 1:
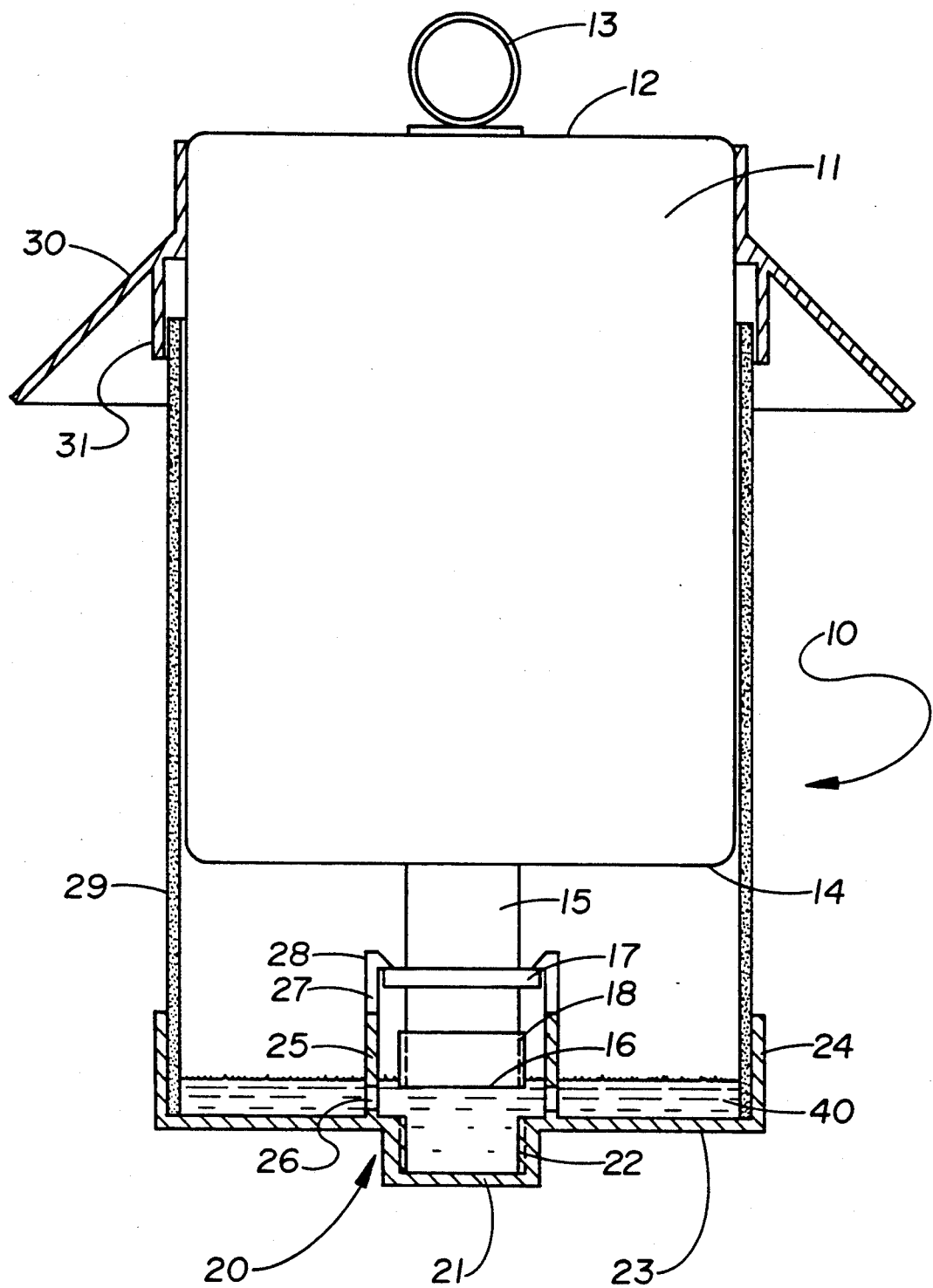
FIG. 1 is a cross-section of a diffuser according to the invention serving for destruction of insects, in the operational state.

The diffuser 10 shown in FIG. 1 comprises a container 11 for holding the liquid to be diffused, made of a material resistant to the chemicals present in the liquid. End wall 12 of container 11 which in operation forms the top is fitted with an integral ring by which the device can be suspended during operation. Container 11 may be cylindrical or have any suitable cross-sectional shape such as, for example, rectangular. Additionally, if desired the container may also be spherical.

Extending from end wall 14 which in operation forms the bottom wall of container 11, is a neck portion 15 having a discharge opening 16 and an exterior annular stop member 17. The end part 18 of the neck portion 15 is externally screw-threaded.

Figure 2:
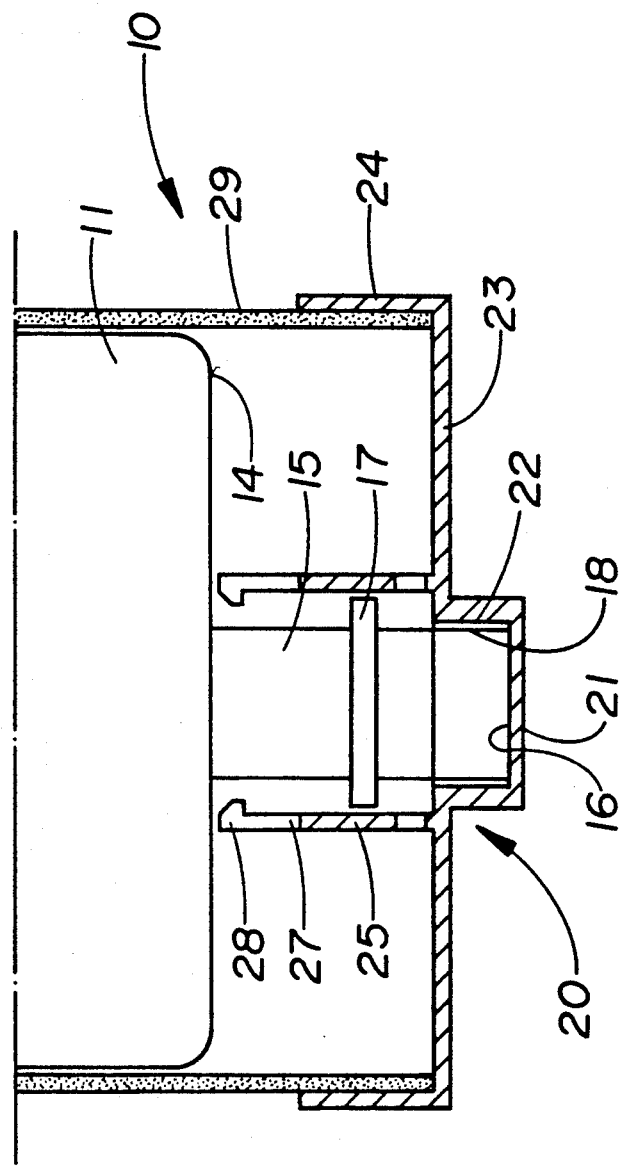
FIG. 2 is a fragmentary cross-section of the diffuser of FIG. 1 in the sealed state.

The diffuser 10 has a base portion 20 comprising an internally screw-threaded cap 21 whose screw thread is adapted to engage the externally screw-threaded end part 18 of the container's neck portion 15 and thereby tightly seal the discharge opening 16 as shown in FIG. 2. Cap 21 is made integral with a dish 23 which has a peripheral, upward extending skirt 24. On its inner side base portion 20 has an integral sleeve 25 with a plurality of ports 26 and upright stays 27 each of which latter comprises a hooked head portion 28 adapted to engage the annular stop member 17 in the manner shown in FIG. 1.

The device 10 according to the embodiment shown in FIG. 1 further comprises a cylindrical absorber body 29 which forms a sleeve around part of container 11 and is axially reciprocable between the sealed state shown in FIG. 2 in which cap 21 is screwed onto neck portion 16 and the operational stage shown in FIG. 1 in which the cap is clear of the neck portion and stay 27 engage the stop member 17 in the manner shown in FIG. 1. The cylindrical absorber body 29 reaches beyond end wall 14 of container 1 into dish 23 and is connected to the skirt 24 thereof. The absorber body 29 may be made of any suitable material such as a high density (e.g. 8 BSR) open celled polyurethane, such as that sold commercially by RECTICELL (trade name).

Near end wall 12 which in operation forms the top container 11 comprises an integral slanted shade 30 which protects the absorber body 29 from rain which may wash off the liquid and against direct insolation. Shade 30 is fitted with a depending annular skirt 31 which serves as guide during the axial reciprocation of the absorber body 29.

During storage and transport cap 21 is screwed on the end part 18 of neck portion 15 whereby the discharge opening 16 is tightly sealed. In this state the containers can be stored and shipped with either of end walls 12 and 14 up, without any danger of spilling.

For operation, the cap 21 is unscrewed and base portion 20 is drawn away from end wall 14 into the position shown in FIG. 1 in which stay 27 engages stop member 17. Liquid is now discharged through opening 16 into the space confined by sleeve 25 and cap 21 and spreads across ports 26 to fill the entire dish 23 in the manner shown in FIG. 1. Absorber body 29 withdraws the liquid from dish 23 and after a while it becomes entirely soaked thereby. Where the device is used for destroying insects the liquid may comprise an insecticide and an insect attracting agent, e.g. a nutrient such as sugar or a pheromone. The insect will be attracted to the absorber body by the fumes of the attracting agent and when contacting the absorber body, it will be poisoned by the insecticide.

If it is desired to interrupt the operation before complete discharge of liquid from container 12 base portion 20 is raised and cap 21 is screwed on whereby the state of FIG. 2 is restored.

During operation the diffuser 10 can be suspended from any suitable holding means by means of ring 13.

Figure 3:
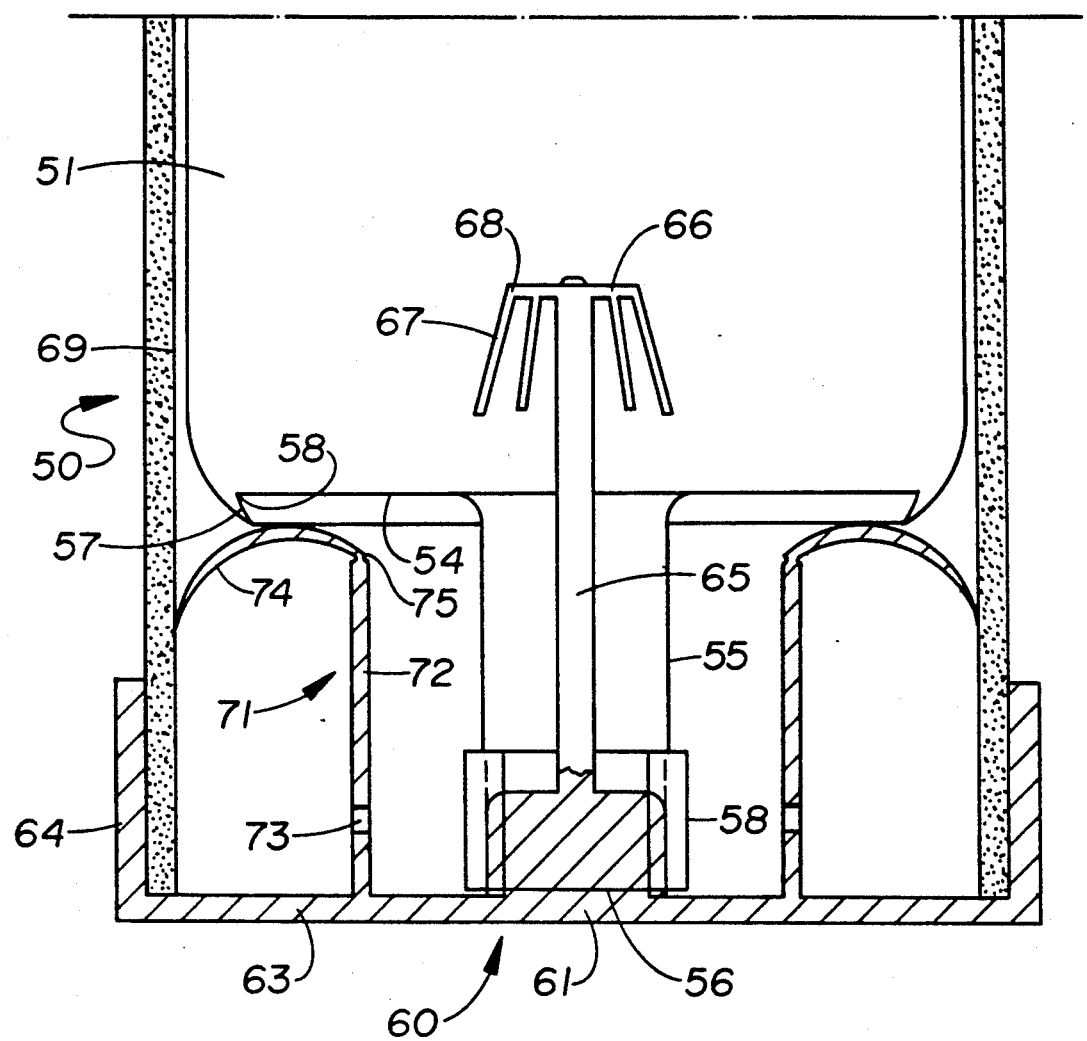
FIG. 3 is a fragmentary cross-section of another embodiment of a diffuser in accordance with the invention in a sealed state.
Figure 4:
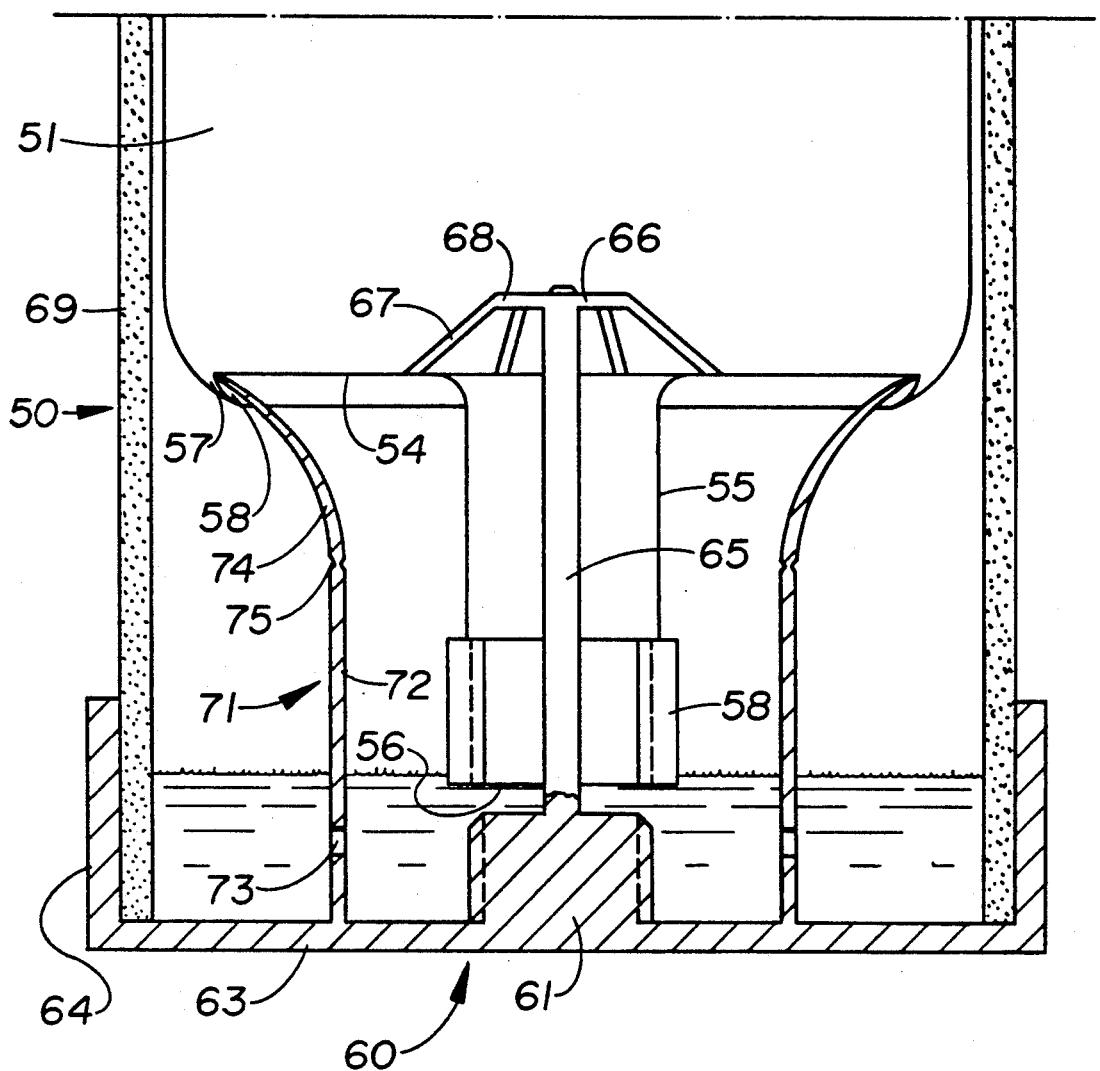
FIG. 4 is a fragmentary cross-section of the diffuser of FIG. 3 in the operational state.

Reference is made now to FIGS. 3 and 4 which show a diffuser advice in accordance with another embodiment of the present invention. The diffuser 50 comprises a container 51 which similarly as in the embodiment of FIGS. 1 and 2 may be cylindrical or have any other suitable shape.

Extending from the end wall portion 54, which in operation constitues the bottom wall of container 51, is a neck portion 55 having a discharge opening 56. The end part 58 of the neck portion 55 is internally screw-threaded. The end wall portion 54 further comprises an integral annular protrusion 57 defining an annular groove 58.

The diffuser has a base portion 60 comprising an externally screw-threaded bulge 61 whose screw-thread is adapted to engage the internally screw-threaded end part 58 of neck portion 55 and thus forms a plug which tightly seals the discharge opening 56. Bulge 61 is integral with a dish 63 which has a peripheral, upward extending skirt 64. Extending upwards from bulge 61 is a shaft 65 having at its top a disk 66 with a plurality of radial stays 67 which are directed downward with a slant and which are pliably attached to the disk at 68 in a manner which allows them a limited vertical pivoted movement about the place of attachment 68 with disk 66. Disk 66 has a smaller diameter than the internal diameter of neck portion 55 which enables its initial insertion into the container.

The device according to FIGS. 3 and 4 further comprise a cylindrical absorber 69 similarly as in the embodiment of the device shown in FIGS. 1 and 2.

The base portion 60 has integral upright support-space means 71 consisting of a sleeve 72 having a plurality of ports 73 which enable the spreading of the liquid discharged from discharge opening 56 to fill the entire dish 63. Sleeve 72 has attached at its top a plurality of flaps 74 which are pliably attached to sleeve 72 at 75 in a manner that enables their vertical pivoted movement about the point of attachment 75.

During storage and transport bulge 61 is screwed inside the end part 58 of neck portion 55 whereby the discharge opening 56 is tightly sealed, as shown in FIG. 3. In this state the lower ends of stays 67 are free inside the container and flaps 74 are externally enveloping protrusion 57 of end wall portion 54.

For operation, bulge 61 is unscrewed whereby base portion 60 is drawn away into the position shown in FIG. 4 whereby liquid is discharged from discharge opening 56 and fills the entire dish 63. In this position stays 67 engage the inner central part of end wall 51 and arrests it from further downward movement. In the downward movement of base portion 60, flaps 74 slide over protrusion 57 and move into the position shown in FIG. 4 wherein their upper end rests inside annular groove 58 whereby the base portion is arrested from moving upwards with respect to the container 51. The device in accordance with this embodiment is suitable both for hanging during operation similarly as the device shown in FIGS. 1 and 2 and for placement on its base portion 60 during operation.

A diffuser device according to the invention may be disposable or designed for repeated use.

We claim:

1. A liquid diffuser device comprising in combination:
a liquid holding container having a neck portion extending from an end wall which in operation constitutes the bottom, which neck portion has a discharge opening;
a base portion including means for tightly sealing the discharge opening of the neck portion of the container, the said means being integral with a skirted dish;
the base portion being associated with the container, such that the base portion and the liquid holding container are slidably longitudinally movable relative to one another for movement between an uppermost position wherein the means for tightly sealing the discharge opening on the base portion engages and tightly seals the discharge opening, so that the flow of liquid from the container through the neck portion is prevented and a lowermost position wherein the means for tightly sealing the discharge opening is spaced from the discharge opening, so that the flow of fluid through the discharge opening is permitted, the base portion further including an upright retainer means integral with said base portion and designed to engage stop means in said container, whereby said skirted dish is arrested in a lowermost position in which the skirted portion of said dish further extends above the discharge opening of said neck portion; and an absorbent material body one end of which is in said skirted dish.

2. A device according to claim 1, wherein the absorbent material body is a sleeve that envelopes the container.

3. The device of claim 1, wherein the means for tightly sealing the discharge opening of the neck portion includes the neck portion having an external screw thread formed therein, and a cap formed on the base portion, the cap having an internal screw thread formed therein, so that the cap is adapted for engagement with the external screw thread of the neck portion, thereby sealing the discharge opening.

4. The device of claim 1, wherein the means for tightly sealing the discharge opening of the neck portion includes the neck portion having an internal screw thread formed therein and a bulge formed on the base portion, the bulge having a shape and diameter corresponding to the internal diameter of the neck portion, the bulge being externally screw threaded and adapted for engagement with the internal screw thread of the neck portion, thereby sealing the discharge opening.

5. The device of claim 1, wherein upright stays are integrally formed with the base portion, the stays including a hooked head portion adapted to engage an annular stop member that is integrally formed with the neck portion.

6. The device of claim 1, further comprising a shaft extending through the neck portion, the shaft having one end that is positioned inside the container and radial stays that extend from the one end of the shaft and which are adapted for engagement with the end wall, whereby the skirted dish is arrested in a lowermost position.

7. The device of claim 1, further including means adapted to arrest the upward movement of the skirted dish with respect to the container.

8. The device of claim 1, further including means for providing access to the absorbent material body, whereby the device is adapted for use in destroying insects.

* * * * *